(12) United States Patent
Doyle et al.

(10) Patent No.: US 7,122,496 B2
(45) Date of Patent: Oct. 17, 2006

(54) PARA-XYLENE SELECTIVE ADSORBENT COMPOSITIONS AND METHODS

(75) Inventors: Ruth Ann Doyle, Oswego, IL (US); Bryce A. Williams, Lisle, IL (US); Jeffrey T. Miller, Naperville, IL (US)

(73) Assignee: BP Corporation North America Inc., Warrenville, IL (US)

( * ) Notice: Subject to any disclaimer, the term of this patent is extended or adjusted under 35 U.S.C. 154(b) by 4 days.

(21) Appl. No.: 10/427,879

(22) Filed: May 1, 2003

(65) Prior Publication Data

US 2004/0220047 A1    Nov. 4, 2004

(51) Int. Cl.
*B01J 29/06*    (2006.01)
*B01J 21/00*    (2006.01)

(52) U.S. Cl. .................. 502/71; 502/60; 502/64; 502/71; 502/77

(58) Field of Classification Search ............ 502/60, 502/64, 71, 77
See application file for complete search history.

(56) References Cited

U.S. PATENT DOCUMENTS

| | | | |
|---|---|---|---|
| 2,985,589 A | 5/1961 | Broughton et al. | |
| 3,201,491 A | 8/1965 | Stine et al. | |
| 3,626,020 A | 12/1971 | Neuzil | |
| 3,696,107 A | 10/1972 | Neuzil | |
| 3,699,182 A | 10/1972 | Cattanach | |
| 3,700,589 A | 10/1972 | Symoniak et al. | |
| 3,702,886 A | 11/1972 | Argauer et al. | |
| 3,729,523 A | 4/1973 | Grandio, Jr. et al. | |
| 3,790,471 A | 2/1974 | Argauer et al. | |
| 3,960,520 A | 6/1976 | Allen | 95/88 |
| 4,039,599 A | 8/1977 | Gewartowski | |
| 4,098,836 A | 7/1978 | Dywer | |
| 4,176,053 A | 11/1979 | Holcombe | |
| 4,184,943 A | 1/1980 | Anderson | |
| 4,210,771 A | 7/1980 | Holcombe | |
| 4,372,022 A | 2/1983 | Puckett | |
| 4,374,022 A | 2/1983 | Fuderer | |
| 4,381,419 A | 4/1983 | Wylie | |
| 4,402,832 A | 9/1983 | Gerhold | |
| 4,476,345 A | 10/1984 | Gray, Jr. et al. | |
| RE31,782 E | 12/1984 | Olson et al. | |
| 4,508,841 A * | 4/1985 | Onuma et al. | 502/73 |
| 4,582,815 A | 4/1986 | Bowes | |
| 4,595,490 A | 6/1986 | Gray, Jr. et al. | |
| 4,705,909 A | 11/1987 | Yan | |
| 4,709,117 A | 11/1987 | Gray, Jr. | |
| 4,760,040 A * | 7/1988 | Sato et al. | 502/68 |
| 4,857,084 A | 8/1989 | Robbins et al. | |
| 4,899,011 A | 2/1990 | Chu et al. | |
| 4,908,342 A | 3/1990 | McWilliams et al. | |
| 5,011,296 A | 4/1991 | Bartosiak et al. | |
| 5,028,573 A | 7/1991 | Brown et al. | |
| 5,118,896 A * | 6/1992 | Steigelmann et al. | 585/467 |
| 5,202,516 A * | 4/1993 | Lee et al. | 585/467 |
| 5,329,060 A | 7/1994 | Swift | |
| 5,367,099 A | 11/1994 | Beck et al. | |
| 5,367,100 A * | 11/1994 | Gongwei et al. | 585/640 |
| 5,448,005 A | 9/1995 | Eccli et al. | |
| 5,460,796 A | 10/1995 | Verduijn | |
| 5,506,182 A * | 4/1996 | Yamagishi et al. | 502/66 |
| 5,516,956 A | 5/1996 | Abichandani et al. | |
| 5,614,079 A * | 3/1997 | Farnos et al. | 208/27 |
| 5,849,258 A * | 12/1998 | Lujano et al. | 423/700 |
| 5,866,740 A | 2/1999 | Mikitenko et al. | |
| 5,908,967 A | 6/1999 | Benazzi et al. | |
| 6,040,257 A * | 3/2000 | Drake et al. | 502/64 |
| 6,084,143 A * | 7/2000 | Girotti et al. | 585/467 |
| 6,111,161 A | 8/2000 | MacPherson et al. | |
| 6,114,592 A | 9/2000 | Gajda et al. | |
| 6,147,272 A | 11/2000 | Mikitenko et al. | |
| 6,150,292 A | 11/2000 | Merlen et al. | |
| 6,150,293 A | 11/2000 | Verduijn et al. | |
| 6,171,370 B1 * | 1/2001 | Hirano et al. | 95/96 |
| 6,183,539 B1 * | 2/2001 | Rode et al. | 95/117 |
| 6,569,400 B1 * | 5/2003 | Sterte et al. | 423/700 |
| 6,723,862 B1 * | 4/2004 | Shuguang et al. | 554/125 |
| 2002/0013216 A1* | 1/2002 | Broekhoven et al. | 502/64 |
| 2002/0065444 A1 | 5/2002 | Deckman et al. | |
| 2002/0068844 A1 | 6/2002 | Williams et al. | |
| 2002/0077519 A1 | 6/2002 | Miller et al. | |
| 2002/0099251 A1 | 7/2002 | Doyle et al. | |
| 2002/0107427 A1 | 8/2002 | Doyle et al. | |

FOREIGN PATENT DOCUMENTS

| | | |
|---|---|---|
| CN | 1105906 | 8/1995 |
| CN | 1136549 A | 11/1996 |

(Continued)

OTHER PUBLICATIONS

T. Boger et al., "The Selective Separation of P-and M-Xylol Over Zeolitic Adsorbents, In The Gas Phase," Chem. Ing. Tech. 69:475-480 (1997).

(Continued)

*Primary Examiner*—Elizabeth D. Wood
(74) *Attorney, Agent, or Firm*—Thomas A. Yassen

(57) ABSTRACT

Adsorbent compositions for vapor-phase adsorption processes, which are selective for para-xylene. Such compositions can be used in gas-phase adsorption processes for the separation of para-xylene or the separation of para-xylene and ethylbenzene from mixed xylenes or a $C_8$ aromatic mixture, respectively. The adsorbent compositions generally comprise materials of a molecular sieve material and a binder, wherein the adsorbent composition has a macropore volume of at least about 0.20 cc/g and a mesopore volume of less than about 0.20 cc/g.

79 Claims, 4 Drawing Sheets

FOREIGN PATENT DOCUMENTS

| | | |
|---|---|---|
| EP | D 138 617 | 4/1985 |
| GB | 1 334 243 | 10/1973 |
| GB | 1 420 796 | 1/1976 |
| WO | WO 93/17987 | 9/1993 |
| WO | WO 96/22262 | 7/1996 |
| WO | WO 00/69796 | 11/2000 |
| WO | WO 01/62691 A1 | 8/2001 |
| WO | WO 02/04391 A1 | 1/2002 |

OTHER PUBLICATIONS

Choudary et al., "Single-Component Sorption/Diffusion of Cyclic Compounds from Their Bulk Liquid Phase in H-ZSM-5 Zeolite," Ind. Eng. Chem. Res., 36:1812-1818 (1997).

Flanigen et al., "Silicalite, a new hydrophobic crystalline silica molecular sieve," Nature, 271:512-516 (1978).

Meier et al., "Atlas of Zeolite Framework Types," Fifth Revised Edition, International Zeolite Association (2001).

Murakami et al., eds., "Hydrocarbon Adsorption Characterization of Some High Silica Zeolites," New Developments in Zeolite Science and Technology, Proceedings of the 7th International Zeolite Conference, Aug. 17-22, 1986, pp. 547-554.

Namba et al., "Novel purification method of commercial o- and m-xylenes by shape selective adsorptionon HZSM-5," Microporous Materials, 8:39-42 (1997).

Pezolt et al., "Pressure Swing Adsorption for VOC Recovery at Gasoline Loading Terminals," Environmental Progress, 16:16 (1997).

Sherman, "Synthetic zeolites and other microporous oxide molecular sieves," Proc. Nat'l. Acad. Sci., USA, 96:3471-3478 (1999).

Yan, "Separation of p-Xylene and Ethylbenzene from C8 Aromatics Using Medium-Pore Zeolites," Inc. Eng. Chem. Res., 28:572-576 (1989).

Yang, "Pressure-Swing Adsorption: Principles and Processes," Gas Separation by Adsorption Process, Butterworth Publishers, Boston, Table of Contents and pp. 237-274 (1987).

ASTM International, "D4926-89(2001) Standard Test Method for Gamma Alumina Content in Catalysts," www.astm.org/cgi-bin/SoftCart.exe, no date.

Quantachrome Instruments, "Mercury Porosimeters—Principle of Operation," www.quantachrome.com/Mercury/Porosimeter-Theory.htm (1999).

Catapal™ Alumina, Material Safety Data Sheet, (SASOL North America Inc.) (2001).

Alcoa, Material Safety Data Sheet, "Pseudoboehmite and Boehmite Alumina," (2002).

Bulletin, "ISOMAR™ Process," UOP LLC (1999).

Bulletin, "Parex™ Process," UOP LLC (1999).

* cited by examiner

PARA-XYLENE SELECTIVE ADSORBENT COMPOSITIONS AND METHODS

BACKGROUND OF THE INVENTION

1. Field of the Invention

The invention relates generally to adsorbent compositions, and in particular to adsorbent compositions which are selective for para-xylene and are useful for vapor-phase adsorption processes.

2. Brief Description of Related Technology

Hydrocarbon mixtures or fractions containing $C_{8+}$ aromatics are often by-products of certain oil refinery processes including, but not limited to, catalytic reforming processes. These hydrocarbon mixtures typically contain up to about 30 weight percent (wt. %) $C_{9+}$ aromatics, up to about 10 wt. % non-aromatics, up to about 50 wt. % ethylbenzene, with the balance (e.g., up to about 100 wt. %) being a mixture of xylene isomers. Most commonly present among the $C_8$ aromatics are ethylbenzene ("EB"), and xylene isomers, including meta-xylene ("mX"), ortho-xylene ("oX"), and para-xylene ("pX"). Typically, when present among the $C_8$ aromatics, ethylbenzene is present in a concentration of up to about 20 wt. % based on the total weight of the $C_8$ aromatics. The three xylene isomers typically comprise the remainder of the $C_8$ aromatics, and are typically present at an equilibrium weight ratio of about 1:2:1 (oX:mX:pX, respectively). Thus, as used herein, the term "equilibrated mixture of xylene isomers" refers to a mixture containing the isomers in the weight ratio of about 1:2:1 (oX:mX:pX).

Efficient separation of the $C_8$ aromatics fraction into its individual constituents is of interest because the individual, isolated $C_8$ aromatic constituents are useful commodity chemicals. For example, ethylbenzene is useful in making styrenes; meta-xylene is useful in making isophthalic acids; ortho-xylene is useful in making phthalic anhydrides; and, para-xylene is useful for making terephthalic acids, which are useful for the synthesis of many commercially important resins, including polyesters such as polybutene terephthalate, polyethylene terephthalate, and polypropylene terephthalate.

However, simply separating the $C_8$ aromatics made available from a particular source may not provide sufficient quantities of a desired $C_8$ aromatic constituent to meet market requirements. For example, it is generally desirable to increase or maximize para-xylene production from a particular $C_8$ aromatic mixture because there is generally a higher demand for para-xylene when compared with the other $C_8$ aromatic constituents. Thus, separation of para-xylene is often coupled with isomerization of the remaining stream containing the meta- and ortho-xylene isomers to convert a portion of the meta- and ortho-xylene isomers to the desired para-xylene by reestablishing the equilibrium between the xylene isomers. Conventional $C_8$ aromatic separation methods may further include a method for the conversion of ethylbenzene into benzene, which can be more easily separated from the xylene isomers by distillation.

Typically, such a hydrocarbon mixture is passed through a separation or fractionation column to remove higher boiling $C_{9+}$ hydrocarbons. A second, lower-boiling fraction can be, removed from a preceding or subsequent column so that the remaining fraction is predominantly a $C_8$ aromatic hydrocarbon mixture.

In general, para-xylene is recovered by subjecting the $C_8$ aromatic mixture to one or more separation steps. Performing fractional distillation on the $C_8$ aromatic mixture is impractical because ethylbenzene, meta-xylene, ortho-xylene, and para-xylene have similar boiling points (falling between about 136° C. and about 144° C.). Thus, separation of para-xylene is generally done by crystallization and/or liquid-phase adsorption chromatography.

Crystallization processes exploit the differences in freezing or crystallization temperatures of the various xylenes—para-xylene crystallizes at about 13.3° C. while ortho-xylene and meta-xylene crystallize at about −25.2° C. and about −47.9° C., respectively. In the physical system of the three xylene isomers, there are two binary eutectics of importance: the para-xylene/meta-xylene binary eutectic and the para-xylene/ortho-xylene binary eutectic. As para-xylene crystallizes from the mixture, the remaining mixture approaches one of these binary eutectics, depending upon the starting composition of the mixture. Therefore, in commercial-scale processes, para-xylene is crystallized such that the binary eutectics are approached—but not reached—to avoid co-crystallization of the other xylene isomers, which would lower the purity of the obtained para-xylene. Because of these binary eutectics, the amount of para-xylene recoverable per pass through a crystallization process is generally no greater than about 65% of the amount of para-xylene present in the stream fed to the crystallization unit. Furthermore, crystallization can be very expensive because the various xylene isomers crystallize at very low temperatures.

U.S. Pat. No. 5,329,060 to Swift (Jul. 12, 1994) discloses increasing recovery of para-xylene by separating the xylene isomers in an adsorption step prior to crystallization. Swift discloses that liquid phase adsorption is preferred because of the reduced temperature requirements and decreased opportunities for side reaction. In the adsorption step, a crystalline zeolitic aluminosilicate adsorbent having a silicon to aluminum ratio between about two and about six selectively adsorbs meta-xylene and ortho-xylene (or alternatively para-xylene) to provide a para-xylene-enriched stream, which is subsequently directed to a crystallization apparatus. The para-xylene lean stream is generally pressurized and reacted in the presence of an isomerization catalyst to obtain an equilibrated mixture of xylene isomers, which can then be recycled to the liquid adsorber.

Liquid-phase adsorption chromatography refers to chromatographic processes in which a mixture comes into contact with a stationary phase and a liquid mobile phase. Separation of the mixture components occurs because of the differences in affinity of the components for the stationary and mobile phases of the chromatographic system. Liquid-phase adsorption chromatographic separations are typically batch processes. Simulated moving bed adsorption chromatography (SiMBAC) is a continuous operation that utilizes the same principles to achieve separation. SiMBAC, however, has its limits and is expensive to operate because it requires an internal recycle of large volume(s) of various hydrocarbon desorbent material(s). Additionally, the effluent streams from the adsorption step must be separated from the desirable products in downstream distillation steps. Thus, conventional liquid-phase adsorption chromatographic processes are disadvantageous because of significant capital and energy costs.

It has been found that the foregoing crystallization and SiMBAC steps can be made more attractive if the feedstock(s) for those steps were reformulated to contain a higher-than-equilibrium concentration of para-xylene. Higher-than-equilibrium concentrations of para-xylene may be obtained by selective toluene disproportionation as described in, for example, International (PCT) Publication Nos. WO 00/69796 (Nov. 23, 2000) and WO 93/17987 (Sep. 16, 1993).

Additionally, crystallization and SiMBAC steps can be designed and operated to concentrate para-xylene streams for subsequent purification steps. However, such concentration steps typically suffer from many (or all) of the disadvantages previously discussed with respect to crystallization and SiMBAC processes.

Feedstocks with higher-than-equilibrium para-xylene concentrations may also be produced by vapor-phase adsorption processes, including pressure swing adsorption ("PSA") processes. PSA processes have been widely practiced for the separation of gases, such as, air into nitrogen and oxygen, removal of water from air, and hydrogen purification, and are generally described in Ralph T. Yang, "Gas Separation by Adsorption Processes," pp. 237–274 (Butterworth Publishers, Boston, 1987) (TP242.Y36). PSA processes generally use a solid adsorbent that preferentially adsorbs some components from a mixture over other components in the mixture. Typically, the total pressure of the system is reduced to recover the adsorbate. In contrast, partial pressure swing adsorption (PPSA) operates at a substantially non-decreasing pressure and uses an inert gas, such as hydrogen or nitrogen, to purge or sweep the adsorbate from the adsorbent. Thus, PPSA processes are based on swings in "partial" pressure, rather than lowering the total unit pressure, as is traditionally practiced with PSA processes. Thermal swing adsorption (TSA) processes are gas-phase adsorption processes, wherein the adsorbate is recovered by raising the temperature of the adsorbent bed. Typically, adsorbate recovery is accomplished by purging the bed with a preheated gas.

Chinese Patent Publication No. 1,136,549 A (Nov. 27, 1996) to Long et al. discloses a method of producing para-xylene by passing a gaseous $C_8$ hydrocarbon mixture through an adsorption bed containing an adsorbent that is selective for para-xylene and ethylbenzene to obtain, after suitable desorption, a stream containing meta-and ortho-xylenes and a stream containing para-xylene and ethylbenzene. The adsorption is carried out at a temperature between 140° C. and 370° C., a pressure between atmospheric pressure and 300 kilopascals (kPa), and using a Mobil-5 (MFI) type molecular sieve adsorbent, including ZSM-5 (available from ExxonMobil Chemicals), ferrierite, and silicalite-1 zeolite molecular sieves, and in particular, binder-free silicalite-1 zeolite molecular sieves. The desorption of the para-xylene and ethylbenzene can be carried out with an aqueous vapor desorbent at a temperature within the same range of the adsorption, and at a pressure between atmospheric and 1000 kPa. Alternatively, the desorption can be carried out without a desorbent, and accomplished by mere decompression at a pressure between 1 kPa and 4 kPa.

SUMMARY

The invention is directed to adsorbent compositions for vapor-phase adsorption processes, and adsorption processes selective for para-xylene. In one embodiment, the adsorbent compositions suitable for vapor-phase adsorption processes comprise materials of a molecular sieve material and a binder, wherein the adsorbent composition has a macropore volume of at least about 0.20 cubic centimeters per gram (cc/g) and a mesopore volume of less than about 0.20 cc/g.

In an alternative embodiment, the adsorbent compositions comprise a molecular sieve material and a binder selected from the group consisting of clays, silicas, silicates, zirconias, titanias, aluminas, and aluminum phosphates, wherein the adsorbent composition has a volumetric ratio of macropores to mesopores of at least about 2.

In another embodiment, the adsorbent compositions comprise a molecular sieve material, wherein the adsorbent composition has a macropore volume of at least about 0.20 cc/g, the adsorbent composition has a mesopore volume of less than about 0.20 cc/g, and the adsorbent composition has less than about 2 wt. % of materials consisting of gamma-alumina.

In yet another embodiment, the adsorbent compositions comprise a molecular sieve material, wherein the adsorbent composition has a volumetric ratio of macropores to mesopores of at least about 2 and the adsorbent composition has less than about 2 wt. % of materials consisting of gamma-alumina.

The invention also is directed to methods of making para-xylene selective adsorbents. In one embodiment according to this aspect of the invention, the method comprises forming a powder from a composition comprising a molecular sieve material, forming an aqueous mixture from the powder, extruding the mixture to form an extrudate, and drying the extrudate to form an adsorbent having a macropore volume of at least about 0.20 cc/g and a mesopore volume of less than about 0.20 cc/g.

In another embodiment, the method comprises forming a powder from a composition comprising a molecular sieve material, forming an aqueous mixture from the powder, extruding the mixture to form an extrudate, and drying the extrudate to form an adsorbent having a volumetric ratio of macropores to mesopores of at least about 2.

In an additional refinement, the invention is directed to adsorption processes which are selective for para-xylene. In one embodiment, the method comprises contacting a mixture comprising xylene isomers with a para-xylene selective adsorbent comprising a molecular sieve material and a binder and desorbing from the para-xylene selective adsorbent an effluent comprising a para-xylene enriched product, wherein the adsorbent has a macropore volume of at least about 0.20 cc/g and a mesopore volume of less than about 0.20 cc/g.

Additional features of the invention should become apparent to those skilled in the art from a review of the following detailed description, taken in conjunction with the drawings, the examples, and the appended claims.

BRIEF DESCRIPTION OF THE DRAWINGS

For a more complete understanding of the invention, reference should be made to the following detailed description and accompanying drawings wherein.

Figure 1:
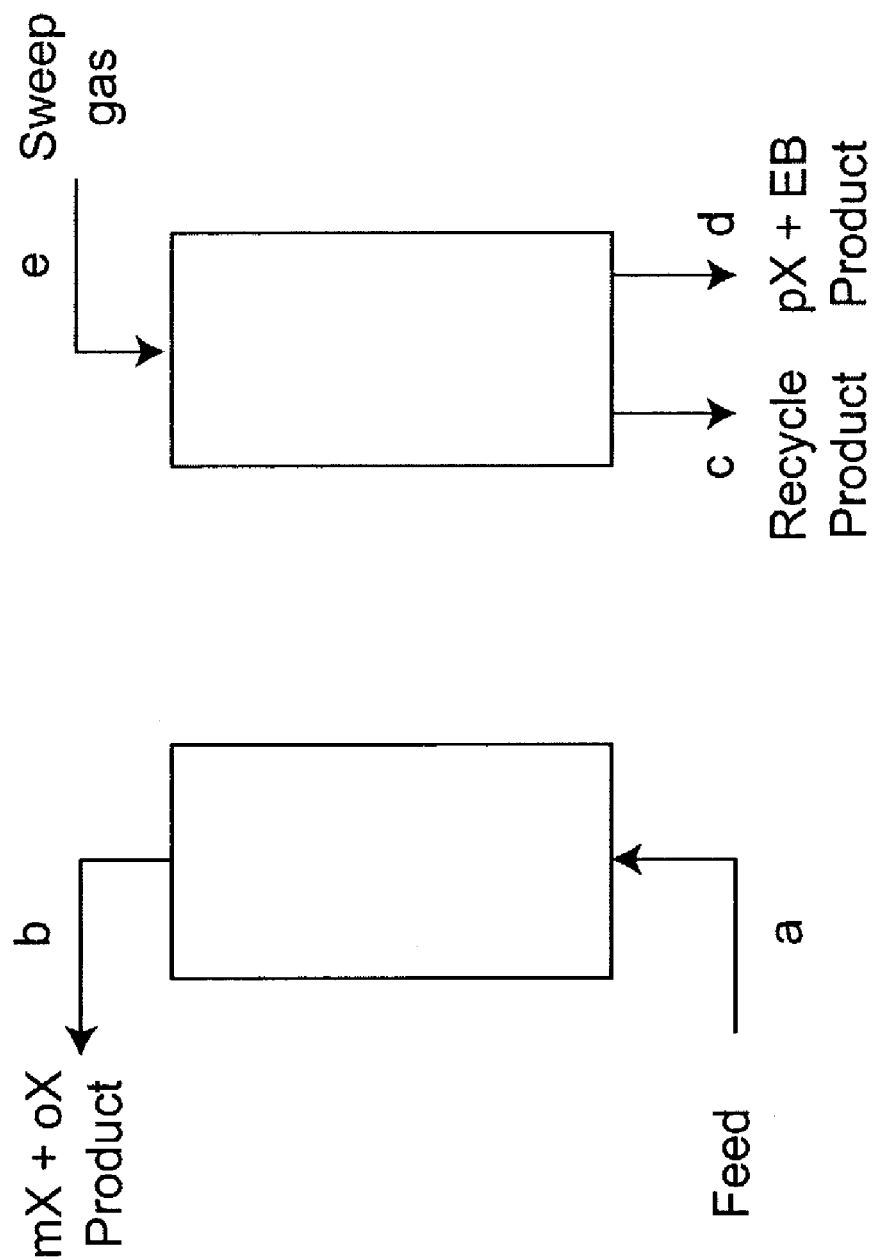
FIG. 1 shows a typical two-bed adsorption system, which can be adapted to utilize the adsorbent compositions and methods in accordance with the invention.

While specific embodiments of the invention are illustrated in the drawings and will hereafter be described, the disclosure is intended to be illustrative, and is not intended to limit the invention to the specific embodiments described and illustrated herein.

DETAILED DESCRIPTION

The invention provides adsorbent compositions for vapor-phase adsorption processes, and adsorption processes selective for para-xylene. Generally, the adsorbent compositions in accordance with the invention comprise a molecular sieve material and a binder.

In one embodiment, the adsorbent compositions comprise a molecular sieve material and a binder, wherein the adsorbent composition has a macropore volume of at least about 0.20 cc/g and a mesopore volume of less than about 0.20 cc/g.

Ranges can be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," the particular value forms another embodiment.

In an alternative embodiment, the adsorbent compositions comprise a molecular sieve material and a binder selected from the group consisting of clays, silicas, silicates, zirconias, titanias, aluminas, and aluminum phosphates, wherein the adsorbent composition has a volumetric ratio of macropores to mesopores of at least about 2.

In another embodiment, the adsorbent compositions comprise a molecular sieve material, wherein the adsorbent composition has a macropore volume of at least about 0.20 cc/g, the adsorbent composition has a mesopore volume of less than about 0.20 cc/g, and the adsorbent composition has less than about 2 wt. % of materials consisting of gamma-alumina.

In yet another embodiment, the adsorbent compositions comprise a molecular sieve material, wherein the adsorbent composition has a volumetric ratio of macropores to mesopores of at least about 2 and the adsorbent composition has less than about 2 wt. % of materials consisting of gamma-alumina.

The invention also provides methods of making para-xylene selective adsorbents. In one embodiment according to this aspect of the invention, the method comprises forming a powder from a composition comprising a molecular sieve material, forming an aqueous mixture from the powder, extruding the mixture to form an extrudate, and drying the extrudate to form an adsorbent having a macropore volume of at least about 0.20 cc/g and a mesopore volume of less than about 0.20 cc/g.

In another embodiment, the method comprises forming a powder from a composition comprising a molecular sieve material, forming an aqueous mixture from the powder, extruding the mixture to form an extrudate, and drying the extrudate to form an adsorbent having a volumetric ratio of macropores to mesopores of at least about 2.

In an additonal refinement, the invention provides adsorption processes which are selective for para-xylene. In one embodiment, the method comprises contacting a mixture comprising xylene isomers with a para-xylene selective adsorbent comprising a molecular sieve material and a binder and desorbing from the para-xylene selective adsorbent an effluent comprising a para-xylene enriched product, wherein the adsorbent has a macropore volume of at least about 0.20 cc/g and a mesopore volume of less than about 0.20 cc/g.

A formed adsorbent composition (e.g., extrudates or pellets) is typically preferred for commercial applications. Powdered molecular sieve is generally not used as an adsorbent for such separations due to large pressure drop and bed fluidization.

As used herein, mesopore refers to a pore of an adsorbent in accordance with the invention which has a radius less than about 600 angstroms (Å). Analogously, as used herein, macropore refers to a pore of an adsorbent having a radius in excess of about 600 Å.

Adsorbents having a macropore volume of at least about 0.20 cc/g and a mesopore volume of less than about 0.20 cc/g are useful for the subject para-xylene selective adsorption processes. Further, adsorbents having a volumetric ratio of macropores to mesopores of at least about 2 have also been found to be effective for such separations.

Molecular Sieve Materials

Preferably, the adsorbents comprise molecular sieve materials that selectively adsorb para-xylene within the channels and pores of the molecular sieve material, while not effectively adsorbing meta-xylene and ortho-xylene (i.e., exclusion of the larger meta-xylene and ortho-xylene or much slower adsorption of the other xylene isomers compared to para-xylene). Molecular sieve materials useful for the separation of para-xylene or of para-xylene and ethylbenzene from mixed xylenes or a mixture of $C_8$ aromatics, respectively, have been described in U.S. Patent Publication 2002/0107427 (Jul. 10, 2001), the entire disclosure of which is hereby incorporated herein by reference.

Generally, the term "molecular sieve" includes a wide variety of natural and synthetic crystalline porous materials having channels, cages, and cavities of molecular dimensions. Molecular sieves include aluminosilicates (zeolites), aluminophosphates, and related materials such as silicoaluminophosphates. Aluminosilicates (zeolites) are typically based on silica tetrahedra in combination with other tetrahedrally substituted elements such as aluminum, boron, titanium, iron, gallium, and the like. Aluminophosphates are based on phosphate tetrahedra in combination with other tetrahedrally substituted elements such as aluminum.

Representative aluminosilicates for use in the adsorbent compositions in accordance with the invention can be described by the following unit cell formula (I):

$M_{x/n}[(A)_x(B)_yO_{2x+2y}]$, wherein M is a compensating cation, n is the cation valence, A is a Group IIIA element, B is a Group IVA element, and y/x is at least about one. Representative Group IIIA elements include trivalent elements, such as, for example, boron, aluminum, and gallium. Representative Group IVA elements include tetravalent elements, such as, for example, silicon and germanium. Titanium is another tetravalent element that can be substituted into the aluminosilicate framework structure, and thus, can be considered to be a Group IVA element, with respect to the above unit cell formula. Typically, the Group IIIA element is aluminum and the Group IVA element is silicon.

Aluminosilicate molecular sieves can be considered as originating from a $SiO_2$ (silica) lattice. Substitution of Group IIIA elements, such as, for example, aluminum, for silicon in the aluminosilicate molecular sieve structure produces a negative framework charge, which must be balanced with a compensating cation. When a Group IIIA element is substituted in the molecular sieve framework, the sieve should be exchanged with a non-acidic counter-ion, such as sodium, to provide a substantially non-acidic sieve. Suitable molecular sieves are preferably substantially non-acidic because adsorbent compositions in accordance with the invention should not possess catalytic isomerization or conversion activity with respect to the $C_8$ aromatic feedstream. For purposes of the subject invention, a molecular sieve which is not catalytically reactive will preferably exhibit less than 10% conversion of para-xylene to meta-xylene or ortho-xylene, more preferably less than 5% conversion, and most preferably less than 1% conversion, at the temperature of operation for the para-xylene separation processes which utilize the adsorbent compositions in accordance with the invention.

The ratio y/x in the unit cell formula (I) provides an indication of various molecular sieve properties, including acidity and hydrophobicity/hydrophilicity. As the ratio y/x increases, the acidity and hydrophilicity of the sieve material decreases. The ratio y/x of molecular sieve materials for use in the invention generally is greater than one. Preferably, the ratio y/x is at least about 200, more preferably at least about 500, and most preferably at least about 1000.

Molecular sieves suitable for use as adsorbents in accordance with the invention include zeolitic materials containing pore dimensions in the range of 5 Å to 6 Å, preferably 5.1 Å to 5.7 Å, and more preferably 5.3 Å to 5.6 Å. These materials typically contain 10-ring tetrahedra structures, and are generally referred to as "medium pore zeolites." Suitable medium pore molecular sieves include, but are not limited to, sieves having a structure type selected from the group consisting of Mobil-twenty three (MTT), ferrierite (FER), Edinburgh University-one (EUO), Mobil-fifty seven (MFS), theta-one (TON), aluminophosphate-eleven (AEL), new-eighty seven (NES) and others with similar pore sizes, as classified in Meier and Olson, "Atlas of Zeolite Framework Types," International Zeolite Association (2001). Preferably, the molecular sieve material is selected from Mobil-Five (MFI) and Mobil-eleven (MEL) structural types. More preferably, the molecular sieve material is of the MFI structural type.

Preferred molecular sieves for use in the adsorbent compositions include ZSM-5 (MFI structure type), ZSM-11 (MEL structure type), and related isotypic structures. Furthermore, the molecular sieve material can comprise silicalite. More preferably, the molecular sieve material can comprise silicalite-1. Silicalites (molecular sieves having the MFI structure type) are essentially all silica molecular sieves, containing minimal amounts of aluminum or other elements.

Small pore molecular sieves, such as type A zeolite, which contain 8-ring structures do not have a sufficiently large pore opening to effectively adsorb para-xylene within the sieve. Most large pore molecular sieves containing 12-ring structures, such as mordenite, Beta, LTL, or Y zeolite, do not selectively adsorb para-xylene with respect to ortho-xylene and meta-xylene without post synthetic modification such as selectivation, ion-exchange, etc. However, several 12-ring structures, having a smaller effective pore size, for example, because of ring puckering, are useful in the adsorbent compositions according to the invention. Such useful large pore molecular sieves include Mobil-twelve (MTW), and aluminophosphate-thirty one (ATO) structure types. ZSM-12 is an example of a suitable sieve material having the MTW framework and AlPO-31 is an example of a suitable sieve material having the ATO framework. Additionally, post-synthetic treatments of 12-ring molecular sieves can be used to achieve para-xylene selectivity increases beyond those observed in the as-synthesized materials. For example, Y or X zeolites ion exchanged to the potassium or barium form have exhibited xylene selectivities for liquid-phase SiMBAC processes. Such modified molecular sieves of the faujasite (FAU) framework would also be suitable for use in the invention.

MFI and MEL sieves (and sieves having the framework structures listed above) can be used to the extent they are substantially non-catalytically active. MFI-based molecular sieves are especially preferred. Silicalite, more specifically, silicalite-1, is most preferred. Silicalites (a molecular sieve having the MFI structure type) are essentially all silica molecular sieves, containing minimal amounts of aluminum or other substituted elements. Preferably, the silicon/aluminum ratio of suitable silicalites is at least about 200, and more preferably at least about 500. The silicon/aluminum ratio of adsorbent compositions in accordance with the invention can suitably be greater than about 1000.

Binder

The adsorbent compositions can contain 100% molecular sieve. Generally, however, the adsorbent compositions also include a binder material. Binder materials are generally employed to impart certain desirable properties to formed adsorbent compositions (e.g., improved crush strength). Suitable binders are selected from the group consisting of clays, silicas, silicates, zirconias, titanias, aluminas, silica-aluminas, silica-magnesias, silica-zirconias, silica-thorias, silica-beryllias, silica-titanias, silica-alumina-thorias, silica-alumina-zirconias, silica-alumina-magnesias, silica-magnesia-zirconias, aluminum phosphates, and mixtures thereof. Preferably, the binder is selected from the group consisting of clays, silicas, silicates, zirconias, titanias, and mixtures thereof.

The adsorbent compositions may also comprise zeolite bound zeolites. In this embodiment of the subject adsorbent compositions, zeolite core crystals are bound by smaller zeolite binder crystals. One procedure for making zeolite-bound zeolite involves converting the silica initially present as silica binder in a silica-bound zeolite aggregate to a zeolite binder (i.e., the silica binder is a zeolitic precursor). The procedure involves aging the silica bound aggregate for sufficient time in an aqueous alkaline solution. During the aging, the amorphous silica surrounding the matrix zeolite crystals is typically converted into zeolite crystals of the same type as the matrix zeolite. Alternatively the silica binder may be converted to crystals which are a crystallographic match for the initially bound zeolite, provided both materials are selective for para-xylene. The newly-formed zeolite crystals surrounding the initial matrix crystals are generally much smaller than the matrix crystals, e.g., of sub-micron size. For the purposes of the subject invention, the term binder includes such zeolite binders.

Typically, the binder comprises up to about 50 wt. % of the composition, based on the total weight of the adsorbent composition. Preferably, the binder comprises about 5 wt. % to about 40 wt. %, more preferably about 10 wt. % to about 30 wt. % of the composition, and most preferably about 20 wt. % of the adsorbent composition.

The binder content of the adsorbent compositions in accordance with the invention can also be expressed as a weight ratio of molecular sieve material to binder. Preferably, the weight ratio of molecular sieve material to binder is at least about one, more preferably at least about three, and most preferably at least about four.

The adsorbent compositions in accordance with the invention are preferably substantially free of gamma-alumina. In the context of this invention, "substantially free of gamma-alumina" means that the adsorbent compositions contain less than about 2 wt. % of materials consisting of gamma-alumina, based on the total weight of the composition. More preferably, the adsorbent compositions contain less than about 1 wt. %, and most preferably less than about 0.20 wt.

% of materials consisting of gamma-alumina. Gamma-alumina content can be measured by ASTM Test Method D4926-89 (2001).

Furthermore, the adsorbent compositions preferably contain less than about 2 wt. %, more preferably less than about 1 wt. %, and most preferably less than about 0.20 wt. % of materials consisting of alumina. In yet a further refinement, the adsorbent compositions preferably have less than about 2 wt. %, more preferably less than about 1 wt. %, and most preferably less than about 0.20 wt. % of materials consisting of $Al_2O_{(3-x)}(OH)_{2x}$, wherein x ranges from 0 to about 0.8. Such materials generally include aluminas and activated aluminas, i.e., thermal decomposition products of aluminum trihydroxides, oxide hydroxides, and nonstoichiometric gelatinous hydroxides. Clays comprising aluminas and/or activated aluminas are not excluded by the foregoing disclosure.

Methods of Making Adsorbent Compositions

The invention provides methods for making para-xylene selective adsorbent compositions in accordance with the invention. According to one embodiment, para-xylene selective adsorbents are prepared by forming a powder from a composition comprising a molecular sieve material, forming an aqueous mixture from the powder, extruding the mixture to form an extrudate, and drying the extrudate to form an adsorbent in accordance with the invention.

Adsorbent Composition Properties

The para-xylene selectivity and the throughput of the adsorbent compositions in accordance with the invention were unexpectedly improved by increasing the pore volume due to large transport-type macropores (pores having a radius in excess of about 600 Å), while decreasing the pore volume due to smaller mesopores (pores having a radius less than about 600 Å). Similarly, the selectivity and the throughput of adsorbent compositions in accordance with the invention were unexpectedly improved when the ratio of macropore volume to mesopore volume is increased. Porosimetry measurements were made on the adsorbent compositions using a Quantachrome Poremaster 60 porosimeter as described in Example 12.

The macropore and mesopore volumes of an adsorbent composition can be altered by standard means which are known to those of ordinary skill in the art. Macropore and mesopore volume can be affected by, for example, changing the binder and/or adding a pore former to the adsorbent composition prior to extrusion. The use of more porous binders, such as for example binders consisting of gamma-alumina, typically increases the macropore volume of the disclosed adsorbents. Adsorbent macropore volume can also be increased by adding pore formers such as $Na_2CO_3$ to the adsorbent composition prior to extrusion.

Preferably, the macropore volume of the adsorbent composition is greater than about 0.20 cc/g, more preferably greater than about 0.30 cc/g, and most preferably greater than about 0.35 cc/g. Preferably, the mesopore volume of the adsorbent compositions is less than about 0.20 cc/g, more preferably less than about 0.15 cc/g, and most preferably less than about 0.10 cc/g. Adsorbents having a macropore volume of greater than about 0.35 cc/g and a mesopore volume of less than about 0.10 cc/g are particulary preferred (e.g., see the adsorbent composition of Example 7 which has a macropore volume of about 0.40 cc/g and a mesopore volume of about 0.05 cc/g.)

Increasing the ratio of macropore volume to mesopore volume provides increased selectivity and throughput to the adsorbent compositions in accordance with the invention. Preferably, the adsorbent compositions have a volumetric ratio of macropores to mesopores of at least about two, more preferably at least about five, and most preferably at least about 10.

Increased throughput (as measured by grams feed per grams formed adsorbent per hour) is an additional benefit realized from increasing the macropore pore volume in the adsorbent compositions in accordance with the invention. The throughput of a formed adsorbent composition determines the amount of adsorbent needed to process a given amount of a $C_8$ hydrocarbon mixture. Accordingly, increasing the throughput results in smaller adsorbent composition loadings and reduced capital cost.

Para-xylene Separation Processes

The invention provides methods for effecting separations of para-xylene (or para-xylene and ethylbenzene) from mixed xylenes (or a $C_8$ aromatic mixture, respectively), which utilize the para-xylene selective adsorbents in accordance with the invention. The adsorbent compositions can be used to effect separations in gas-phase adsorption processes, e.g., in any vapor phase swing adsorption process. Accordingly, pressure swing adsorption units, partial pressure swing adsorption units, and thermal swing adsorption units can be used to practice the inventive methods.

According to one embodiment, the method comprises contacting a feed mixture comprising xylene isomers with a para-xylene selective adsorbent in accordance with the invention and desorbing from the para-xylene selective adsorbent an effluent comprising a para-xylene enriched product.

Preferably, the contacting step is carried out at an operating temperature between about 145° C. and about 400° C. and/or at an operating pressure between about 345 kPa and about 6895 kPa. More preferably, the contacting step is carried out at an operating temperature between about 200° C. and about 300° C. and/or at an operating pressure between about 448 kPa and about 2068 kPa. It is particularly preferred that the operating temperature is isothermal and/or the operating pressure is isobaric.

Generally, the desorbing step comprises feeding a sweep gas into a bed. Typically, the desorbing step is carried out at an operating temperature between about 145° C. and about 400° C., and/or an operating pressure between about 345 kPa and about 6895 kPa. More preferably, the desorbing step is carried out at an operating temperature between about 200° C. and about 300° C. and an operating pressure between about 448 kPa and about 2068 kPa.

The method may further include contacting the mixture with the adsorbent to obtain a para-xylene depleted raffinate and isomerizing at least a portion of the para-xylene depleted raffinate to obtain a hydrocarbon mixture comprising equilibrated xylene isomers. The hydrocarbon mixture comprising equilibrated xylene isomers and generated by an isomerization step is preferably combined with at least a portion of the feed mixture comprising xylene isomers.

Adsorbent compositions in accordance with the invention also can be used in a non-decreasing total pressure/swinging partial pressure method of adsorbing para-xylene from a feed of $C_8$ aromatics comprising xylene isomers, wherein an adsorbed para-xylene enriched product is desorbed and collected, and an unadsorbed (para-xylene depleted) portion of the feed is isomerized to produce an equilibrated mixture of xylene isomers, which can be combined with the feed. A more detailed description of the method is set forth in U.S. Patent Publication 2002/0107427 (Jul. 10, 2001). One embodiment of that method generally includes contacting at a substantially non-decreasing total pressure a gaseous mixture comprising xylene isomers and ethylbenzene with a para-xylene selective adsorbent to obtain a para-xylene depleted raffinate and a desorption effluent comprising a para-xylene enriched product. The method also includes isomerizing at least a portion of the para-xylene depleted raffinate. The isomerization step includes isomerizing the para-xylene depleted raffinate to obtain a hydrocarbon mixture comprising equilibrated xylene isomers. To increase the yield of para-xylene, a portion of the equilibrated xylene isomers obtained by way of isomerization can be combined with the mixture before contacting the adsorbent (i.e., recycled).

EXAMPLES

The following examples are provided to illustrate the invention, but are not intended to limit the scope thereof. Example 1 is directed to the preparation of suitable molecular sieve materials for use in the adsorbent compositions according to the invention. Example 2 is directed to a general procedure for preparing the adsorbent compositions in accordance with the invention. Examples 3–11 are directed to specific procedures for preparing the adsorbent compositions in accordance with the invention. Example 12 is directed to a procedure for measuring and calculating the porosity of an adsorbent composition in accordance with the invention. Example 13 sets forth experimental results (e.g., selectivity and throughput) for the adsorbent compositions of Examples 3–11.

Example 1

Silicalite can be prepared from a variety of standard procedures. Using a representative procedure, 18.4 grams sodium hydroxide (NaOH) was added to 227.6 grams of water. After dissolution of the NaOH, 12.8 grams tetrapropylammonium bromide (TPABr) and 122.6 grams Nalco 2327 silica sol (40 wt. % silica) was added to the solution, and the solution was stirred for two hours. Concentrated sulfuric acid ($H_2SO_4$) was slowly added to the mixture to achieve a pH of 13. The resulting solution was heated under autogenous pressure in a TEFLON®-lined autoclave for one to seven days at 300° F. (149° C.). The crystals were filtered and washed to a neutral pH filtrate. In place of calcining, the molecular sieve was dried at 329° F. (165° C.) for 4 hours.

Example 2

Adsorbent compositions in accordance with the invention were generally made by mixing the components described in the following Examples.

More specifically, molecular sieve material, prepared and dried as in Example 1, was ground into a fine, uniform powder. Binders and pore formers were optionally added. Appropriate quantities of water were added to the powder (which optionally may further include one or more binders and one or more pore formers) to form an aqueous mixture capable of being processed with a 4 inch single screw pin extruder having a 1/16 inch die. Small quantities of the mixture were introduced into the extruder opening. The extrudates were initially dried at 329° F. (165° C.) for 4 hours, and subsequently calcined at 950° F. (510° C.) for 4 hours to remove the organic template ion from the molecular sieve pores.

Example 3

An adsorbent composition in accordance with the invention was produced by combining 80 wt. % silicalite molecular sieve (prepared in accordance with Example 1) with 20 wt. % of a calcium-exchanged clay. A suitable calcium-exchanged clay is montmorillonite grade F-2 (Engelhard Corporation, New Jersey).

Example 4

An adsorbent composition in accordance with the invention was produced by combining 80 wt. % silicalite molecular sieve (prepared in accordance with Example 1) with 20 wt. % of a synthetic, layered silicate. A suitable synthetic, layered silicate is ECS-3 (Engelhard Corporation, New Jersey).

Example 5

An adsorbent composition in accordance with the invention was produced by combining 80 wt. % silicalite molecular sieve (prepared in accordance with Example 1) with 17 wt. % calcium-exchanged clay and 3 wt. % silica. A suitable silica is CAB-O-SIL® HS-5 (Cabot Corporation, Massachusetts).

Example 6

An adsorbent composition in accordance with the invention was produced by combining 80 wt. % silicalite molecular sieve (prepared in accordance with Example 1), 10 wt. % calcium-exchanged clay and 10 wt. % of a synthetic, layered silicate.

Example 7

An adsorbent composition in accordance with the invention was produced by combining 80 wt. % silicalite molecular sieve (prepared in accordance with Example 1), 10 wt. % calcium-exchanged clay and 10 wt. % pseudo-boehmite alumina. A suitable pseudo-boehmite alumina is Versal™ 300 alumina (UOP LLC, Illinois).

Example 8

An adsorbent composition in accordance with the invention was produced by combining 80 wt. % silicalite molecular sieve (prepared in accordance with Example 1) and 20 wt. % pseudo-boehmite alumina. An additional 5 wt. % of $Na_2CO_3$ was added to the resulting mixture prior to extruding in order to facilitate macropore formation.

Example 9

An adsorbent composition in accordance with the invention was produced by combining 80 wt. % silicalite molecular sieve (prepared in accordance with Example 1) and 20 wt. % bayerite alumina. Suitable bayerite aluminas include Catapal™ B and Pural™ BT aluminas (SASOL North America Inc., Texas).

Example 10

An adsorbent composition in accordance with the invention was produced by combining 80 wt. % silicalite molecular sieve (prepared in accordance with Example 1) with 10 wt. % boehmite alumina and 10 wt. % pseudo-boehmite alumina. A suitable boehmite alumina is Pural™ SB alumina (SASOL North America Inc., Texas).

Example 11

An adsorbent in accordance with the invention was produced by combining 80 wt. % silicalite molecular sieve (prepared in accordance with Example 1) with 20 wt. % pseudo-boehmite alumina. An additional 1 wt. % of $Na_2CO_3$ was added to the resulting mixture prior to extruding in order to facilitate macropore formation.

Example 12

Porosimetry measurements were made using a Quantachrome Poremaster 60 porosimeter (Quantachrome Instruments, Boynton Beach, Fla.). Porosimetry measurements are calculated from the Washburn equation:

$$PD = -4\gamma \cos \theta$$

where P is the applied pressure, D is the diameter, $\gamma$ is the surface tension of mercury (480 dyne $cm^{-1}$) and $\theta$ is the contact angle between mercury and the pore wall.

Approximately 0.3 gram to 0.4 gram samples of adsorbent compositions were dried in a vacuum oven for approximately 12 hours at a temperature ranging from about 140° C. to about 150° C. The mercury surface tension was 480.00 dyne $cm^{-1}$ (may also be expressed as $erg/cm^2$) and the mercury contact angle was 140.0°. The pressure range was 20 psia to 60,000 psia (137.9 kPa to 413,688 kPa). Filling pressure was 14.7 psia (101.4 kPa). The porosimetry results for adsorbent compositions prepared according to Examples 3–11 are listed in Table 1.

TABLE 1

Mercury Porosimetry Results

| Adsorbent Composition | Total Intruded Pore Volume (cc/g) | Pore Volume >600 Å radius (cc/g) | Pore Volume <600 Å radius (cc/g) | Ratio >600 Å/<600 Å |
|---|---|---|---|---|
| Example 3 | 0.27 | 0.21 | 0.06 | 3.5 |
| Example 4 | 0.49 | 0.38 | 0.11 | 3.5 |
| Example 5 | 0.43 | 0.39 | 0.04 | 9.8 |
| Example 6 | 0.51 | 0.36 | 0.15 | 2.4 |
| Example 7 | 0.44 | 0.37 | 0.07 | 5.3 |
| Example 8 | 0.62 | 0.45 | 0.17 | 2.6 |
| Example 9 | 0.51 | 0.35 | 0.16 | 2.2 |
| Example 10 | 0.47 | 0.31 | 0.16 | 1.9 |
| Example 11 | 0.46 | 0.29 | 0.17 | 1.7 |

Example 13

The adsorbent compositions of Examples 3–11 were tested in the two bed adsorption apparatus depicted in FIG. 1, at 195° C. and 35 psia (241.3 kPa), to determine the recovery of para-xylene and ethylbenzene, the selectivity, and the throughput. Results from the experiments are given in Table 3, below.

The composition of the feed stream (a) used in the experiments was 5.37 wt. % ethylbenzene, 22.29 wt. % para-xylene, 49.06 wt. % meta-xylene, and 23.28 wt. % ortho-xylene. The flow rate of the feed stream (a) was adjusted as needed so that 85% recovery was obtained, thereby allowing the adsorbent compositions to be compared on an equal basis. The sweep flow (e) was 15.0 cubic feet of nitrogen per hour at standard conditions (SCFH of nitrogen).

As indicated in FIG. 1, the desorption effluent (c) was collected as a separate product in these experiments. In a commercial unit, stream (c) would normally be recycled to the feed stream (a).

The experiments were performed in accordance with the adsorption/desorption programming schedule set forth in Table 2.

TABLE 2

Two-Bed PPSA Sweep Experiments

| Bed: | 1 | 2 |
|---|---|---|
| Step: | A1 | D1 |
|  | A1 | D2 |
|  | D1 | A1 |
|  | D2 | A1 |

In all experiments, the A1 step time was 64 seconds, the D1 step time was 12 seconds, and the D2 step time was 52 seconds.

As used herein, the recovery of para-xylene (pX) and ethylbenzene (EB) is defined as:

$$pX + EB \text{ Recovery} = \frac{[\text{grams}(pX + EB) \text{ in stream } d]}{\{[\text{grams}(pX + EB) \text{ in stream } a] - [\text{grams}(pX + EB) \text{ in stream } c]\}} \times 100\%$$

As used herein, the selectivity of the adsorbent (at constant feed composition) is defined as:

Selectivity = wt. % para-xylene in stream d + wt. % EB in stream d

As used herein, the throughput of an adsorbent composition is defined as:

$$\text{Throughput} = \frac{(\text{grams HC/hr in stream } a) - (\text{grams HC/hr in stream } c)}{\text{total grams absorbent in both beds}}$$

where HC is the liquid hydrocarbon stream. A more fundamental measure for throughput is based on the weight of the molecular sieve material rather than the weight of formed adsorbent. However, since all of the formed adsorbents in this example contain about 80 wt % sieve, this definition of throughput is essentially equivalent and is directly related to such a fundamental measure.

As used herein, the porosity factor P, a unitless parameter, is defined as:

P = {[(macropore volume)×10] + (ratio macropore volume to mesopore volume)}.

TABLE 3

Two-Bed PPSA Experimental Results

| Example | 3 | 4 | 5 | 6 | 7 | 8 | 9 | 10 | 11 |
|---|---|---|---|---|---|---|---|---|---|
| Weight of Adsorbent, g | 719 | 552 | 560 | 519 | 536 | 481 | 540 | 542 | 577 |
| Feed (a), g/min | 11.8 | 16.2 | 15.9 | 15.6 | 17.0 | 18.4 | 19.5 | 20.6 | 17.2 |
| pX + EB Recovery, % | 83.4 | 86.1 | 85.8 | 86.8 | 82.2 | 86.7 | 84.5 | 85.1 | 91.7 |
| Selectivity, wt. % | 72.6 | 79.9 | 88.5 | 74.2 | 55.3 | 65.0 | 62.6 | 60.5 | 59.9 |
| Throughput | 0.69 | 1.26 | 1.41 | 1.13 | 1.39 | 1.69 | 1.27 | 1.31 | 0.83 |
| Porosity Factor | 5.6 | 7.3 | 13.7 | 6.0 | 9.0 | 7.1 | 5.7 | 5.0 | 4.6 |

Figure 2:
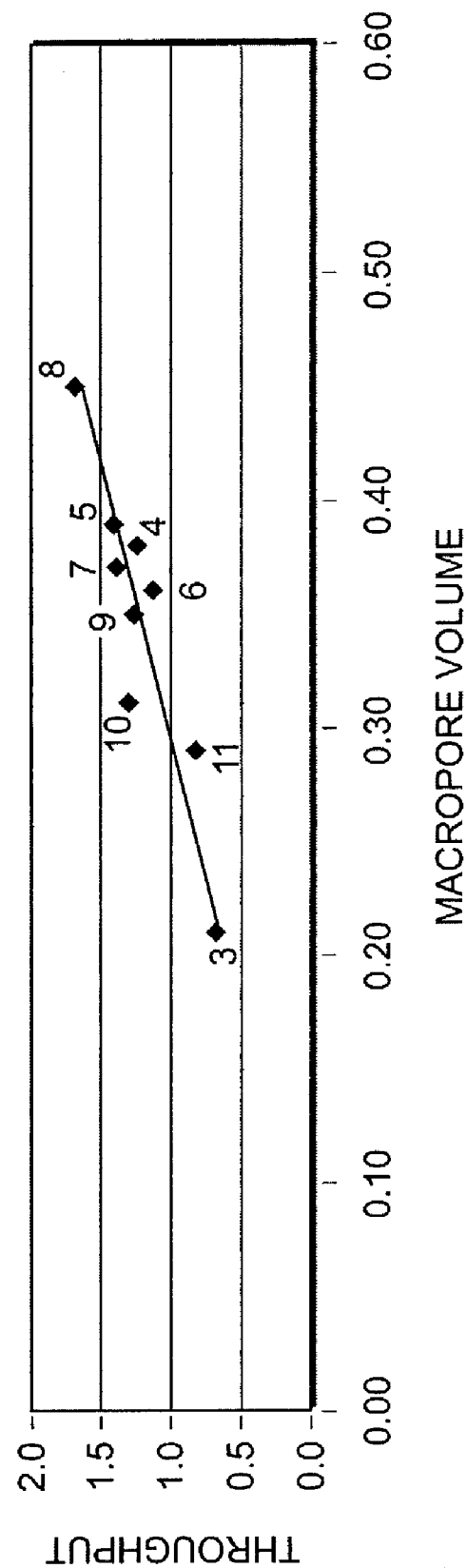
FIG. 2 is a graph of throughput versus macropore volume for the adsorbent compositions of Examples 3–11.

Turning now to the figures, FIG. 2 is a plot of throughput versus macropore volume for the adsorbent compositions of Examples 3–11. FIG. 2 shows that the throughput of the adsorbent compositions is generally increased as the macropore volume of the adsorbent compositions is increased.

Figure 3:
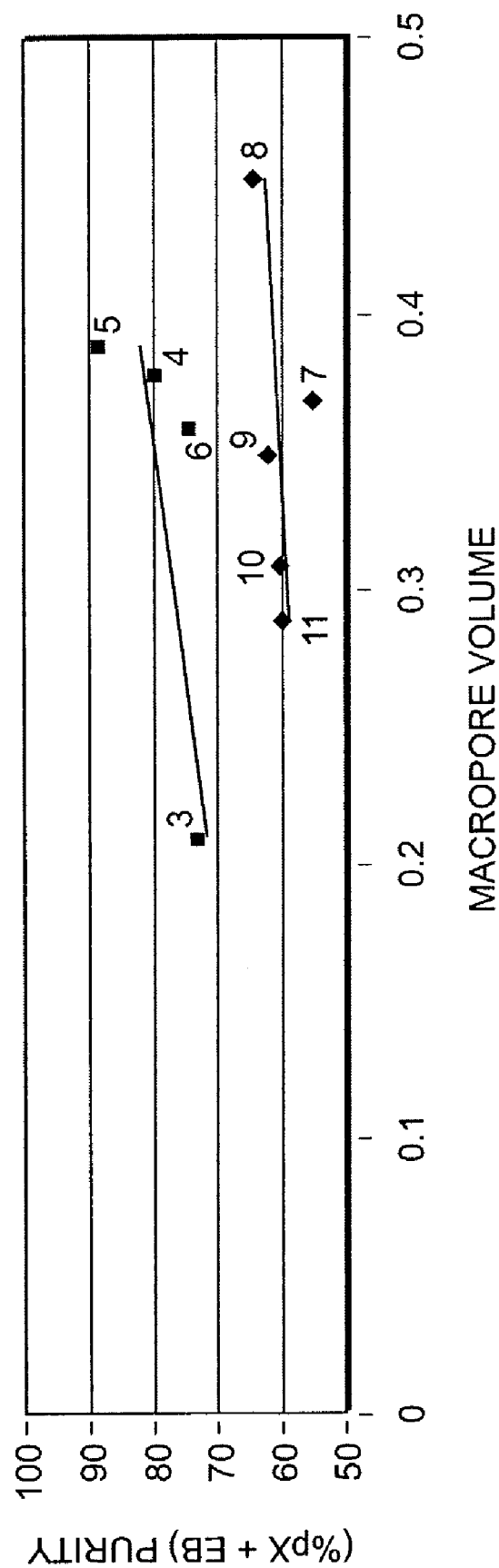
FIG. 3 is a graph of (pX+EB) purity versus macropore volume for the adsorbent compositions of Examples 3–6 in view of a graph showing (pX+EB) purity versus macropore volume for the adsorbent compositions of Examples 7–11; and, FIG. 4 is a graph showing (pX+EB) purity versus P, porosity factor, for the adsorbent compositions of Examples 3–6 in view of a graph showing (pX+EB) purity versus P for the adsorbent compositions of Examples 7–11.

FIG. 3 is a plot of (pX+EB) selectivity versus macropore volume for the adsorbent compositions of Examples 3–6 in view of a plot showing (pX+EB) selectivity versus macropore volume for the adsorbent compositions of Examples 7–11, which contain varying quantities of gamma-alumina. FIG. 3 illustrates that the gamma-alumina-containing adsorbent compositions are less selective for para-xylene than the adsorbent compositions of Examples 3–6, for similar macropore volume values, thereby indicating that the adsorbent compositions should preferably be substantially free of gamma-alumina.

Figure 4:
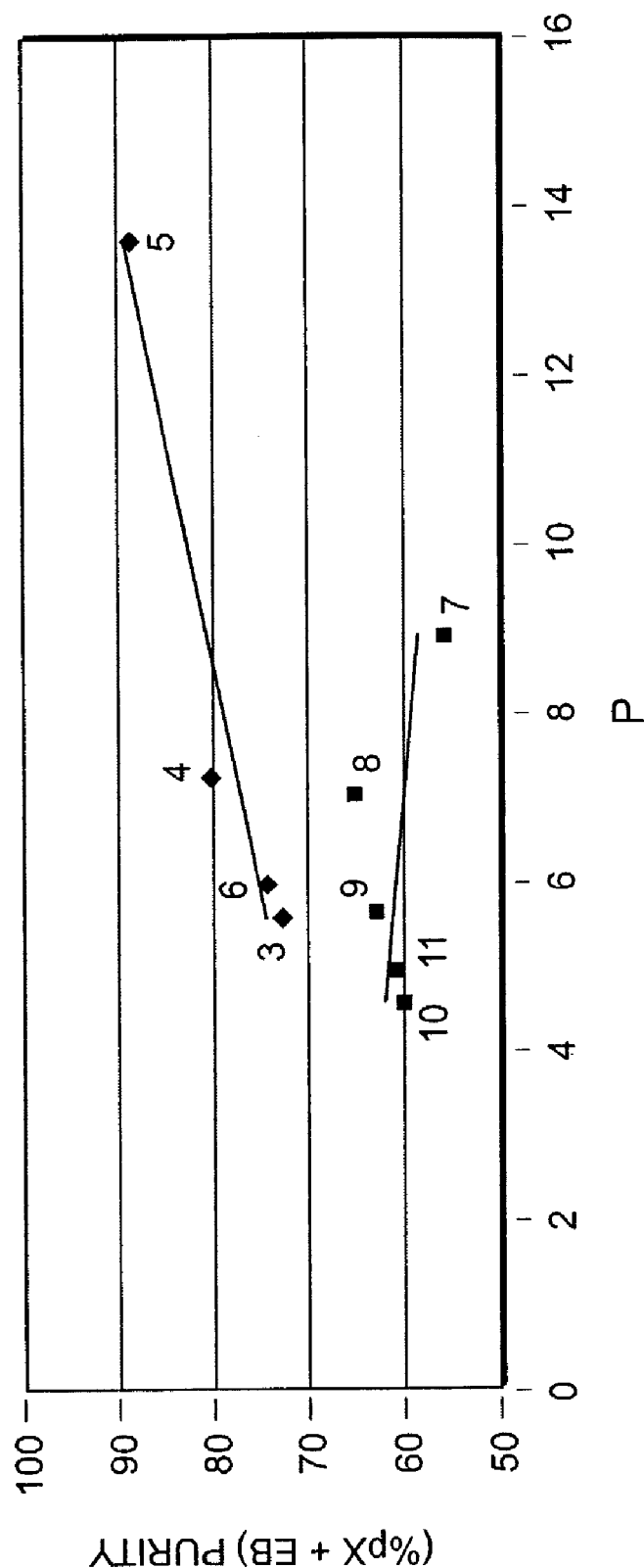

FIG. 4 shows a plot of (pX+EB) purity versus P for the adsorbent compositions of Examples 3–6 in view of a plot showing (pX+EB) purity versus P for the adsorbent compositions of Examples 7–11. FIG. 4 illustrates that the gamma-alumina-containing adsorbent compositions of Examples 7–11 are less selective for para-xylene than the adsorbent compositions of Examples 3–6, for similar P values, thereby illustrating that the alumina-containing adsorbents do not perform separations as well as the adsorbents in accordance with the invention, which do not contain alumina.

Additionally, FIGS. 3 and 4 demonstrate that Example 11, which has a volumetric ratio of macropores to mesopores of less than two, performs relatively unsatisfactorily in separating $C_8$ aromatics. The relatively unsatisfactory performance of this adsorbent is manifested in the combination of relatively low throughput and selectivity values (when compared with the throughput and selectivity values for the adsorbents of the other examples).

What is claimed is:

1. An adsorbent composition comprising:
   (a) a substantially non-catalytically active molecular sieve material capable of selectively adsorbing para-xylene and ethylbenzene from a mixture of $C_8$ aromatics and having a pore size in the range of 5 Å to 6 Å; and,
   (b) a binder,
   wherein the adsorbent composition has a macropore volume of pores having a radius greater than about 600 angstroms of at least about 0.20 cc/g, and a mesopore volume of pores having a radius less than about 600 angstroms of less than about 0.20 cc/g.

2. The adsorbent composition of claim 1, wherein the binder is selected from the group consisting of clays, silicas, silicates, zirconias, titanias, aluminas, and aluminum phosphates.

3. The adsorbent composition of claim 1, wherein the binder comprises up to about 50 wt. % of the composition.

4. The adsorbent composition of claim 1, wherein the macropore volume is at least about 0.30 cc/g.

5. The adsorbent composition of claim 1, wherein the mesopore volume is less than about 0.15 cc/g.

6. The adsorbent composition of claim 1, wherein the weight ratio of molecular sieve material to binder is at least about 1.

7. The adsorbent composition of claim 1, wherein the adsorbent composition has a volumetric ratio of macropores to mesopores of at least about 2.

8. The adsorbent composition of claim 7, wherein the adsorbent composition has a volumetric ratio of macropores to mesopores of at least about 5.

9. The adsorbent composition of claim 1, wherein the adsorbent composition has less than about 2 wt. % of materials consisting of gamma-alumina.

10. The adsorbent composition of claim 9, wherein the adsorbent composition has less than about 2 wt. % of materials consisting of $Al_2O_{(3-x)}(OH)_{2x}$, wherein x ranges from 0 to about 0.8.

11. The adsorbent composition of claim 1, wherein the molecular sieve material has a structural type selected from the group consisting of Mobil-five (MFI), Mobil-eleven (MEL), Mobil-twenty three (MTT), ferrierite (FER), Edinburgh University-one (EUO), Mobil-fifty seven (MFS), theta-one (TON), aluminophosphate-eleven (AEL), new-eighty seven (NES), Mobil-twelve (MTW), and aluminophosphate-thirty one (ATO).

12. The adsorbent composition of claim 11, wherein the molecular sieve material is of the MFI structural type.

13. The adsorbent composition of claim 1, wherein the molecular sieve material is substantially non-acidic.

14. An adsorbent composition comprising:
   (a) a substantially non-catalytically active molecular sieve material capable of selectively adsorbing para-xylene and ethylbenzene from a mixture of $C_8$ aromatics and having a pore size in the range of 5 Å to 6 Å; and,
   (b) a binder selected from the group consisting of clays, silicas, silicates, zirconias, titanias, aluminas, and aluminum phosphates,
   wherein the adsorbent composition has a volumetric ratio of macropores having a radius less than about 600 angstroms to mesopores having a radius less than about 600 angstroms of at least about 2.

15. The adsorbent composition of claim 14, wherein the molecular sieve material has a unit cell formula $M_{x/n}[(A)_x (B)_y O_{2x+2y}]$,
   wherein M is a compensating cation, n is the cation valence, A is a Group IIIA element, B is a Group IVA element, and y/x is at least about one.

16. The adsorbent composition of claim 15, wherein y/x is at least about 500.

17. The adsorbent composition of claim 14, wherein the volumetric ratio of macropores to mesopores is a least about 5.

18. The adsorbent composition of claim 14, wherein the adsorbent composition has a macropore volume of at least about 0.20 cc/g.

19. The adsorbent composition of claim 14, wherein the adsorbent composition has a mesopore volume of less than about 0.20 cc/g.

20. The adsorbent composition of claim 14, wherein the binder comprises up to about 50 wt. % of the composition.

21. The adsorbent composition of claim 14, wherein the weight ratio of molecular sieve material to binder is at least about 1.

22. The adsorbent composition of claim 14, wherein the composition has less than about 2 wt. % of materials consisting of gamma-alumina.

23. The adsorbent composition of claim 22, wherein the composition has less than about 2 wt. % of materials consisting of $Al_2O_{(3-x)}(OH)_{2x}$, wherein x ranges from 0 to about 0.8.

24. The adsorbent composition of claim 14, wherein the molecular sieve material has a structural type selected from the group consisting of Mobil-five (MFI), Mobil-eleven (MEL), Mobil-twenty three (MTT), ferrierite (FER), Edinburgh University-one (EUO), Mobil-fifty seven (MFS), theta-one (TON), aluminophosphate-eleven (AEL), new-eighty seven (NES), Mobil-twelve (MTW), and aluminophosphate-thirty one (ATO).

25. The adsorbent composition of claim 24, wherein the molecular sieve material is of the MFI structural type.

26. The adsorbent composition of claim 14, wherein the molecular sieve material is substantially non-acidic.

27. An adsorbent composition comprising:
a substantially non-catalytically active molecular sieve material capable of selectively adsorbing para-xylene and ethylbenzene from a mixture of $C_8$ aromatics and having a pore size in the range of 5 Å to 6 Å,
wherein the adsorbent composition has a macropore volume of pores having a radius greater than about 600 angstroms of at least about 0.20 cc/g, the adsorbent composition has a mesopore volume of pores having a radius greater than about 600 angstroms of less than about 0.20 cc/g, and the adsorbent composition has less than about 2 wt. % of materials consisting of gamma-alumina.

28. The adsorbent composition of claim 27, wherein the macropore volume is at least about 0.30 cc/g.

29. The adsorbent composition of claim 27, wherein the mesopore volume is less than about 0.15 cc/g.

30. The adsorbent composition of claim 27, wherein the adsorbent composition has less than about 2 wt. % of materials consisting of $Al_2O_{(3-x)}(OH)_{2x}$, wherein x ranges from 0 to about 0.8.

31. The adsorbent composition of claim 27, wherein the adsorbent composition has a volumetric ratio of macropores to mesopores of at least about 2.

32. The adsorbent composition of claim 27, further comprising a binder.

33. The adsorbent composition of claim 32, wherein the binder is selected from the group consisting of clays, silicas, silicates, zirconias, titanias, and aluminum phosphates.

34. The adsorbent composition of claim 32, wherein the binder comprises up to about 50 wt. % of the composition.

35. The adsorbent composition of claim 32, wherein the weight ratio of molecular sieve material to binder is at least about 1.

36. The adsorbent composition of claim 27, wherein the molecular sieve material has a structural type selected from the group consisting of Mobil-five (MFI), Mobil-eleven (MEL), Mobil-twenty three (MTT), ferrierite (FER), Edinburgh University-one (EUO), Mobil-fifty seven (MFS), theta-one (TON), aluminophosphate-eleven (AEL), new-eighty seven (NES), Mobil-twelve (MTW), and aluminophosphate-thirty one (ATO).

37. The adsorbent composition of claim 27, wherein the molecular sieve material is substantially non-acidic.

38. An adsorbent composition comprising:
a substantially non-catalytically active molecular sieve material capable of selectively adsorbing para-xylene and ethylbezene from a mixture of $C_8$ aromatics and having a pore size in the range of 5 Å to 6 Å,
wherein the adsorbent composition has a volumetric ratio of macropores having a radius greater than about 600 angstroms to mesopores having a radius less than about 600 angstroms of at least about 2 and less than about 2 wt. % of materials consisting of gamma-alumina.

39. The adsorbent composition of claim 38, wherein the volumetric ratio of macropores to mesopores is at least about 5.

40. The adsorbent composition of claim 38, wherein the adsorbent composition has less than about 2 wt. % of materials consisting of $Al_2O_{(3-x)}(OH)_{2x}$, wherein x ranges from 0 to about 0.8.

41. The adsorbent composition of claim 38, further comprising a binder.

42. The adsorbent composition of claim 41, wherein the binder is selected from the group consisting of clays, silicas, silicates, zirconias, titanias, and aluminum phosphates.

43. The adsorbent composition of claim 41, wherein the binder comprises up to about 50 wt. % of the composition.

44. The adsorbent composition of claim 41, wherein the weight ratio of molecular sieve material to binder is at least about 1.

45. The adsorbent composition of claim 38, wherein the molecular sieve material has a structural type selected from the group consisting of Mobil-five (MFI), Mobil-eleven (MEL), Mobil-twenty three (MTT), ferrierite (FER), Edinburgh University-one (EUO), Mobil-fifty seven (MFS), theta-one (TON), aluminophosphate-eleven (AEL), new-eighty seven (NES), Mobil-twelve (MTW), and aluminophosphate-thirty one (ATO).

46. The adsorbent composition of claim 38, wherein the molecular sieve material is substantially non-acidic.

47. A method comprising:
(a) forming a powder from a composition comprising a substantially non-catalytically active molecular sieve material capable of selectively adsorbing para-xylene and ethylbenzene from a mixture of $C_8$ aromatics and having a pore size in the range of 5 Å to 6 Å;
(b) forming an aqueous mixture from the powder;
(c) extruding the mixture to form an extrudate; and,
(d) drying the extrudate to form an adsorbent having a macropore volume of pores having a radius greater than about 600 angstroms of at least about 0.20 cc/g and a mesopore volume of pores having a radius less than about 600 angstroms of less than about 0.20 cc/g.

48. The method of claim 47, wherein the composition further comprises a binder.

49. The method of claim 48, wherein the binder is selected from the group consisting of clays, silicas, silicates, zirconias, titanias, aluminas, and aluminum phosphates.

50. The method of claim 48, wherein the binder comprises up to about 50 wt. % of the composition.

51. The method of claim 47, wherein the macropore volume is at least about 0.30 cc/g.

52. The method of claim 47, wherein the mesopore volume is less than about 0.15 cc/g.

53. The method of claim 47, wherein the composition has less than about 2 wt. % of materials consisting of gamma-alumina.

54. The method of claim 53, wherein the adsorbent composition has less than about 2 wt. % of materials consisting of $Al_2O_{(3-x)}(OH)_{2x}$, wherein x ranges from 0 to about 0.8.

55. The method of claim 47, wherein the molecular sieve material has a structural type selected from the group consisting of Mobil-five (MFI), Mobil-eleven (MEL), Mobil-twenty three (MTT), ferrierite (FER), Edinburgh University-one (EUO), Mobil-fifty seven (MFS), theta-one (TON), aluminophosphate-eleven (AEL), new-eighty seven (NES), Mobil-twelve (MTW), and aluminophosphate-thirty one (ATO).

56. The method of claim 55, wherein the molecular sieve material is of the MFI structural type.

57. The method of claim 47, wherein the molecular sieve material is substantially non-acidic.

58. A method comprising:
(a) forming a powder from a composition comprising a substantially non-catalytically active molecular sieve material capable of selectively adsorbing para-xylene and ethylbenzene from a mixture of $C_8$ aromatics and having a pore size in the range of 5 Å to 6 Å;
(b) forming an aqueous mixture from the powder;
(c) extruding the mixture to form an extrudate; and,
(d) drying the extrudate to form an adsorbent having a volumetric ratio of macropores having a radius less than about 600 angstroms to mesopores having a radius less than about 600 angstroms of at least about 2.

59. The method of claim 58, wherein the molecular sieve material has a unit cell formula $M_{x/n}[(A)_x(B)_yO_{2x+2y}]$,
wherein M is a compensating cation, n is the cation valence, A is a Group IIIA element, B is a Group IVA element, and y/x is at least about one.

60. The method of claim 59, wherein y/x is at least about 500.

61. The method of claim 58, wherein the volumetric ratio of macropores to mesopores is at least about 5.

62. The method of claim 58, wherein the composition further comprises a binder.

63. The method of claim 62, wherein the binder is selected from the group consisting of clays, silicas, silicates, zirconias, titanias, aluminas, and aluminum phosphates.

64. The method of claim 62, wherein the binder comprises up to about 50 wt. % of the composition.

65. The method of claim 58, wherein the composition has less than about 2 wt. % of materials consisting gamma-alumina.

66. The method of claim 65, wherein the composition has less than about 2 wt. % of materials consisting of $Al_2O_{(3-x)}(OH)_{2x}$, wherein x ranges from 0 to about 0.8.

67. The method of claim 58, wherein the molecular sieve material has a structural type selected from the group consisting of Mobil-live (MFI), Mobil-eleven (MEL), Mobil-twenty three (MTT), ferrierite (FER), Edinburgh University-one (EUO), Mobil-fifty seven (MFS), theta-one (TON), aluminophosphate-eleven (AEL), new-eighty seven (NES), Mobil-twelve (MTW), and aluminophosphate-thirty one (ATO).

68. The method of claim 67, wherein the molecular sieve material is of the MFI structural type.

69. The method of claim 58, wherein the molecular sieve material is substantially non-acidic.

70. An adsorbent composition comprising:
(a) a molecular sieve material capable of selectively adsorbing para-xylene and ethylbenzene from a mixture of $C_8$ aromatics and having a pore size in the range of 5 Å to 6 Å; and,
(b) a binder,
wherein the adsorbent composition has a macropore volume of pores having a radius greater than about 600 angstroms of at least about 0.20 cc/g, a mesopore volume of pores having a radius less than about 600 angstroms of less than about 0.20 cc/g, and less than about 2 wt. % of materials consisting of $Al_2O_{(3-x)}(OH)_{2x}$, wherein x ranges from 0 to about 0.8.

71. The adsorbent composition of claim 70, wherein the binder is selected from the group consisting of clays, silicas, silicates, zirconias, titanias, aluminas, and aluminum phosphates.

72. The adsorbent composition of claim 70, wherein the binder comprises up to about 50 wt. % of the composition.

73. The adsorbent composition of claim 70, wherein the macropore volume is at least about 0.30 cc/g, and the mesopore volume is less than about 0.15 cc/g.

74. The adsorbent composition of claim 70, wherein the weight ratio of molecular sieve material to binder is at least about 1.

75. The adsorbent composition of claim 70, wherein the adsorbent composition has a volumetric ratio of macropores to mesopores of at least about 2.

76. The adsorbent composition of claim 74, wherein the adsorbent composition has a volumetric ratio of macropores to mesopores of at least about 5.

77. The adsorbent composition of claim 70, wherein the molecular sieve material has a structural type selected from the group consisting of Mobil-five (MFI), Mobil-eleven (MEL), Mobil-twenty three (MTT), ferrierite (FER), Edinburgh University-one (EUO), Mobil-fifty seven (MFS), theta-one (TON), aluminophosphate-eleven (AEL), new-eighty seven (NES), Mobil-twelve (MTW), and aluminophosphate-thirty one (ATO).

78. The adsorbent composition of claim 76, wherein the molecular sieve material is of the MFI structural type.

79. The adsorbent composition of claim 76, wherein the molecular sieve material is substantially non-acidic.

* * * * *